US007348437B2

(12) United States Patent
Cravatt et al.

(10) Patent No.: US 7,348,437 B2
(45) Date of Patent: Mar. 25, 2008

(54) PROTEOMIC ANALYSIS

(75) Inventors: Benjamin F. Cravatt, La Jolla, CA (US); Alan Saghatelian, San Diego, CA (US); Nadim Jessani, Los Altos, CA (US); Arul Joseph, Cambridge, MA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/143,009

(22) Filed: Jun. 1, 2005

(65) Prior Publication Data

US 2005/0266505 A1 Dec. 1, 2005

Related U.S. Application Data

(60) Provisional application No. 60/576,333, filed on Jun. 1, 2004.

(51) Int. Cl.
C07D 249/04 (2006.01)
C07C 233/30 (2006.01)
C07C 233/34 (2006.01)
A61K 31/4192 (2006.01)
A61K 31/191 (2006.01)
A61K 31/192 (2006.01)
A61K 31/194 (2006.01)
A61K 31/195 (2006.01)

(52) U.S. Cl. ............... 548/255; 514/359; 514/575; 564/123

(58) Field of Classification Search ............ 548/255; 514/359, 575; 564/123
See application file for complete search history.

(56) References Cited

U.S. PATENT DOCUMENTS

| | | | |
|---|---|---|---|
| 6,358,980 B1 * | 3/2002 | Levin et al. | 514/330 |
| 6,362,183 B1 | 3/2002 | Freskos et al. | |
| 6,380,258 B2 | 4/2002 | Bedell et al. | |
| 2003/0130257 A1 | 7/2003 | Sheppeck et al. | |

FOREIGN PATENT DOCUMENTS

| DE | 2442124 A1 * | 3/1975 |
|---|---|---|
| WO | WO-02/30873 A1 * | 4/2002 |

OTHER PUBLICATIONS

Saghatelian, Alan et al, "Activity-based probes for the proteomic profiling of metalloproteases," Proceedings of the National Academy of Sciences of the USA (2004), 101(27), pp. 10000-10005.*
Chan, Elaine W.S., "Developing Photoactive Affinity Probes for Proteomic Profiling: Hydroxamate-based Probes for Metalloproteases," Journal of the American Chem. Society (2004), vol. 126, pp. 14435-14446.*
CAPLUS Accession No. 2004:28489, Sewald et al, abstract of "New chemical tools for mechanism-based discovery and profiling of protein families in functional proteomics," Proceedings of the 27$^{th}$ Eur. Peptide Symposium (2002), pp. 406-407.*
CAPLUS Accession No. 2004:28489, Sewald et al, abstract of "New chemical tools for mechanism-based discovery and profiling of protein families in functional proteomics," Proceedings of the 27th Eur. Peptide Symposium (2002), pp. 406-407.*
Adam, G. C, Burbaum, J. J., Kozarich, J. W., Patricelli, M. P., & Cravatt, B. F. (2004) *J. Amer. Chem. Soc.* 126, 1363-1368.
Adam, G. C, Cravatt, B. F., & Sorensen, E. J. (2001) *Chem Biol.* 8, 81-95.
Adam, G. C, Cravatt, B. F., & Sorensen, E. J. (2002) *Nat. Biotechnol.* 20, 805-809.
Adam, G. C, Sorensen, E. J., & Cravatt, B. F. (2002) *Mol. Cell. Proteomics* 1, 781-790.
Adam, G. C, Sorensen, E. J., & Cravatt, B. F. (2002) *Mol. Cell. Proteomics* 1, 828-835.
Bogyo, M. & Wang, E. W. (2002) *Curr. Top. Microbiol. Immunol.* 268, 184-208.
Borodovsky, A., Ovaa, FL, Kolli, N., Gan-Erdene, T., Wilkinson, K.D., Ploegh, H.L., Kessler, B.M. (2002) *Chem. Biol.* 9, 1149-1159.
Brown, S., Bernardo, M. M., Li, Z.-H., Kotra, L. P., Tanaka, Y., Fridman, R., & Mobashery, S. (2000) *J. Amer. Chem. Soc.* 122, 3410-3411.
Chang, C, Werb, Z. (2001) *Trends Cell Biol.* 11, S37-43.
Coleman, J. E. Zinc enzymes. (1998) *Curr. Opin. Chem. Biol.* 2, 222-234.
Coussens, L. M., Fingleton, B., & Matrisian, L. M. (2002) *Science* 295, 2387-2392.
Davenport, R. J., Watson, R. J. An improved synthesis of the broad spectrum matrix metalloprotease inhibitor marimastat. *Tett. Lett.* 41, 7983-7986 (2000).
Dhanaraj, V., Ye, Q.-Z., Johnson, L. L., Hupe, D. J., Ortwine, D. F., Dunbar, J., J.B., Rubin, J. R., Pavlovsky, A., Humblet, C, & Blundell, T. L. (1996) *Structure* 4, 375-386.
Faleiro, L., Kobayashi, R., Fearnhead, H., & Lazebnik, Y. (1997) *EMBO J.* 16, 2271-2281.
Freije, J. R. & Bischoff, R. (2003) *J. Chromatogr. A.* 1009, 3541-3544.
Greenbaum, D., Baruch, A., Hayrapetian, L., Darula, Z., Burlingame, A., Medzihradszky, K. F., & Bogyo, M. (2002) *Mol. Cell. Proteomics* 1, 60-68.
Greenbaum, D., Medzihradszky, K. F., Burlingame, A., & Bogyo, M. (2000) *Chem. Biol.* 7, 569-581.

(Continued)

Primary Examiner—Kamal A. Saeed
Assistant Examiner—Janet L. Coppins
(74) Attorney, Agent, or Firm—DLA Piper US LLP

(57) ABSTRACT

Activity-based compositions for analyzing metalloproteases are disclosed, where the compositions include a chemical compound including a hydroxamate moiety and a benzophenone moiety. Methods for synthesizing these compounds are also disclosed, as well as methods of using them for determining the bioactivity of a compositions comprising active compounds toward a metalloproteases and for determining the potency of an inhibitor against a metalloprotease.

21 Claims, 5 Drawing Sheets

OTHER PUBLICATIONS

Gygi, S. P., Rist, B., Gerber, S. A., Turecek, F., Gelb, M. H., & Aebersold, R. (1999) *Nat. Biotechnol.* 17, 994-999.

Hagenstein, M. C, Mussgnug, J. H., Lotte, K., Plessow, R., Brockhinke, A., Kruse, O., & Sewald, N. (2003) *Angew. Chem. Int. Ed. Engl.* 42, 5635-5638.

Jessani, N. & Cravatt, B. F. (2004) *Curr. Opin. Chem. Biol.* 8, 54-59.

Jessani, N., Liu, Y., Humphrey, M., & Cravatt, B. F. (2002) *Proc. Natl. Acad. Sci. U.S.A.* 99, 10335-10340.

Kanitakis, J., Narvaez, D., & Claudy, A. (2002) *Melanom Res.* 12, 241-244.

Kidd, D., Liu, Y., & Cravatt, B. F. (2001) *Biochemistry* 40, 6107-6115.

Kim, D. H. & Mobashery, S. (2001) *Curr. Med. Chem.* 8, 959-965.

Kobe, B. & Kemp, B. E. (1999) *Nature* 402, 373-376.

Leung, D., Hardouin, C, Boger, D. L., & Cravatt, B. F. (2003) *Nat. Biotechnol.* 21, 687-691.

Levy, D. E., Lapierre, F., Liang, W., Ye, W., Lange, C. W., Li, X., Grobelny, D., Casabonne, M., Tyrrell, D., Holme, K., Nadzan, A., & Galardy, R. E. (1998) *J. Med. Chem.* 41, 199-223.

Li, Yue-Ming, et al. (2000) *Nature* 405, 689-694.

Liu, Y., Patricelli, M. P., & Cravatt, B. F. (1999) *Proc. Natl. Acad. Sci. U.S.A.* 96, 14694-14699.

Marcotte, P. A. et al. (1999) *J. Enzyme Inhib.* 14, 425-435.

Marks, P. A., Richon, V. M., Breslow, R., Rifkind, R. A. (2001) *Curr. Opin. Oncol.* 13, 477-483.

Michnick, S. W. (2004) *Drug Discov. Today* 9, 262-267.

Mikami, Y., Hata, S., Kiyokama, T., & Manabe, T. (2002) *Mod. Pathol.* 15, 923-930.

Nelson, A. R., Fingleton, B., Rothenberg, M. L., & Matrisian, L. M. (2000) *J. Clin. Oncol.* 18, 1135-1149.

Ovaa, H. et al. (2003) *Angew. Chem. Int. Ed. Engl.* 42, 3626-3629.

Overall, C. M. & Lopez-Otin, C. (2002) *Nat. Rev. Cancer* 2, 657-672.

Papandreou, C. N., Usmani, B., Geng, Y., Bogenrieder, T., Freeman, R., Wilk, S., FInstad, C. L., Reuter, V. E., Powell, C. T., Scheinberg, D., Magill, C, Scher, H. I., Albino, A. P., & Nanus, D. M. (1998) *Nat. Med.* 4, 50-57.

Patricelli, M. P., Giang, D. K., Stamp, L. M., & Burbaum, J. J. (2001) *Proteomics* 1, 1067-1071.

Patterson, S. D. & Aebersold, R. (2003) *Nat. Genet.* 33, 311-323.

Patton, W. F., Schulenberg, B., & Steinberg, T. H. (2002) *Curr. Opin. Biotechnol.* 13, 321-328.

Peunte, X. S., Sanchez, L. M., Overall, C. M., & Lopez-Otin, C. (2003) *Nat. Rev. Genet.* 4, 544-558.

Rasnick, D. & Powers, J. C. (1978) *Biochemistry* 17, 4363-4369.

Seftor, E. A., Meltzer, P. S., Kirschmann, D. A., Pe'er, J., Maniotis, A. J., Trent, J. M., Folberg, R., & Hendrix, M. J. (2002) *Clin. Exp. Metastasis* 19, 233-246.

Shipp, M. A., Tarr, G. E., Chen, C.-Y., Switzer, S. N., Hersh, L. B., Stein, H., Sunday, M. E., & Reinherz, E. L. (1991) *Proc. Natl. Acad. Sci. U.S.A.* 88, 10662-10666.

Speers, A. E., Adam, G. C, & Cravatt, B. F. (2003) *J. Amer. Chem. Soc.* 125, 4686-4687.

Speers, A. E. & Cravatt, B. F. (2004) *Chembiochem.* 5, 41-47.

Speers, A. E., Cravatt, B. F. Profiling Enzyme Activities in Vivo Using Click Chemistry Methods. *Chem. Bio.* 11, 535-546.

Troeberg, L. & Nagase, H. (2003) *Methods Mol. Biol.* 225, 77-87.

Turner, A. J., Isaac, R. E., & Coates, D. (2001) *Bioessays* 23, 261-269.

Whittaker, M., Floyd, C. D., Brown, P., & Gearing, A. J. H. (1999) *Chem. Rev.* 99, 2735-2776.

Yamamoto, M., Tsujishita, H., Hori, N., Ohishi, Y., Inoue, S., Ikeda, S., & Okada, Y. (1998) *J. Med. Chem.* 41, 1209-1217.

Yao, T., Takata, M., Tustsumi, S., Nishiyama, K., Taguchi, K., Nagai, E., & Tsuneyoshi, M. (2002) *Pathology* 34, 556-506.

Saghatelian, Alan. "Activity-based probes for the proteomic profiling of metalloproteases." *PNAS*, vol. 101, No. 27, pp. 10000-10005 (2004).

* cited by examiner

PROTEOMIC ANALYSIS

CROSS REFERENCE TO RELATED APPLICATIONS

This application claims the benefit of priority under 35 U.S.C. § 119(e) of patent application U.S. Ser. No. 60/576,333 filed Jun. 1, 2004, the entire content of which is incorporated herein by reference.

GOVERNMENT SUPPORT

This invention was made in part with government support under Contract No. CA87660 by the National Institutes of Health. The United States Government has certain rights in the invention.

FIELD OF THE INVENTION

This invention is related to proteomic analysis, particularly, to the analysis of portions of a proteome containing certain enzymes, such as metalloproteases.

BACKGROUND

Most current conventional methods of the proteome analysis focus on measuring and recording variations in protein level. These approaches are commonly referred to as "proteomics." In general, proteomics seeks to measure the abundance of broad profiles of proteins being present in complex biological mixtures. A major goal of proteomics is to develop global methods for the analysis of protein function in samples of high biological complexity.

In typical proteomic experiments, the expression levels of proteins in cells, tissues, and/or fluids are compared using techniques such as two-dimensional electrophoresis or isotope-coded affinity tagging, where variations in protein abundance are used to infer changes in protein activity. However, many proteins are regulated by a complex array of post-translational mechanisms. For such proteins, alterations in their abundance may not correlate with changes in activity. For example, some proteins, such as metalloproteases (MPs) enzymes, are subject to numerous forms of post-translational regulation in vivo, including production as inactive zymogens and inhibition by endogenous proteins. These post-translational events hinder the functional analysis of MPs using conventional, abundance-based genomic and proteomic methods.

To address the problems that may be caused by the post-translational events, a chemical methodology known as activity-based protein profiling (ABPP) has been introduced. According to the ABPP method, active site-directed probes are used to record variations in the activity of proteins in whole proteomes.

ABPP probes typically include three moieties: a binding group that promotes interactions with the active sites of specific classes of enzymes, a reactive group that covalently labels these active sites, and a reporter group (e.g., fluorophore, biotin) for the visualization and affinity purification of probe-labeled enzymes. ABPP probes are used to tag specific groups of proteins based on functional properties rather than expression level alone, thus providing good access to low abundance proteins in complex proteomes.

The need to devise methods of measuring protein activity, as opposed to abundance are best illustrated in case of enzymes which are an important subset of proteins. Enzymes are known to be key to almost every biologic process, including blood coagulation, inflammation, angiogenesis, neural plasticity, peptide hormone processing and T-lymphocyte-mediated cytotoxicity. Several human diseases are known to be associated with dysfunctions in enzymes. These include, but are not limited to, hemorrhagic disorders, emphysema, arthritis and even to cancer.

To date, ABPP probes have been developed for many biomedically relevant enzyme classes, including serine hydrolases, cysteine proteases, and oxidoreductases, as well as for profiling enzyme activities in living cells and animals. Despite these and other advantages of ABPP over conventional proteomic methods, several important enzyme classes remain unaddressed by this approach. One class of enzymes for which the ABPP method has not been developed includes the metalloproteases (MP) comprising a large and diverse group of enzymes that play key roles in many physiological and pathological processes, such as tissue remodeling, peptide hormone signaling, and cancer.

One approach for the activity-based profiling of proteins that has been used is the creation of ABPP probes designed to target conserved nucleophiles in the protein active sites. For example, this method has been used for some classes of proteases, such as serine or cysteine proteases. However, this technique cannot be directly applied to MPs, which utilize a zinc-activated water molecule (rather than a protein-bound nucleophile) for catalysis. Therefore, an alternative approach is required to generate chemical probes that label the active sites of MPs with sufficient potency and specificity to enable functional profiling of these enzymes in whole proteomes.

In view of the foregoing, an acute need exists to develop activity-based protein profiling methods for metalloproteases. Embodiments of the present invention provide such methods.

SUMMARY

According to an embodiment of the present invention, an activity-based composition for analyzing metalloproteases is provided, the composition comprising a chemical compound including a hydroxamate moiety and a benzophenone moiety. The compound can include at least one additional functional moiety, such as a rhodamine group and/or a biotin group.

According to another embodiment of the present invention, an activity-based composition for analyzing metalloproteases is provided, the composition comprising a chemical compound having the formula (A):

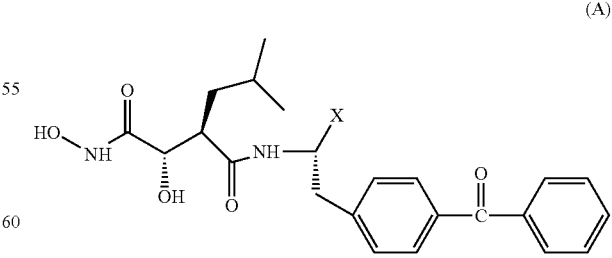

(A)

wherein X is a functional moiety. Examples of the functional group X that can be used include a rhodamine group, and further a biotin group. Examples of particular chemical compounds that can be used include compounds (B) or (C):

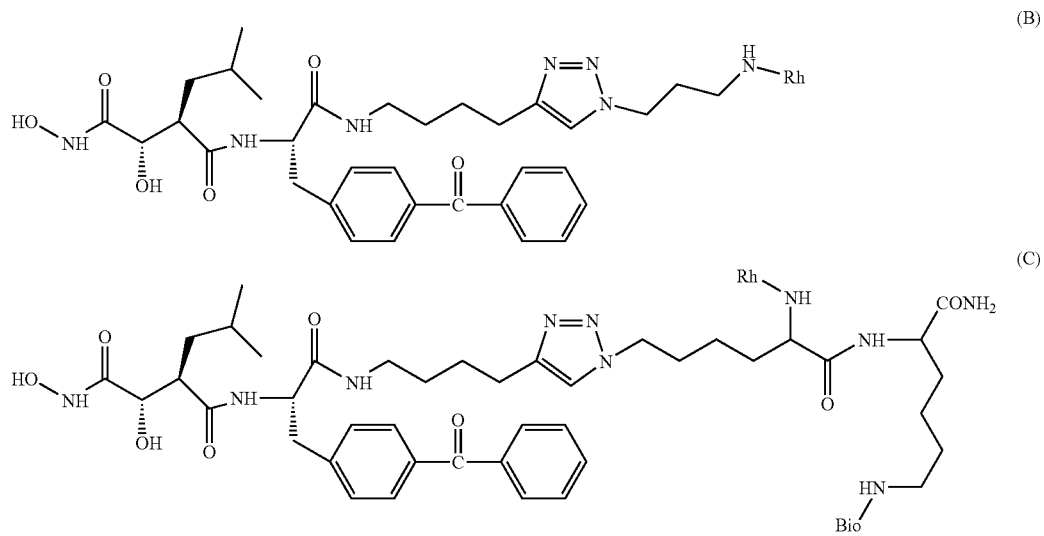

According to yet another embodiment of the present invention, a method for determining the bioactivity of a composition comprising an active compound toward a metalloprotease having an active site is provided, the method including combining the composition with the metalloprotease under conditions suitable for reaction leading to binding the active compound to the active site to form an active compound-metalloprotease adduct, crosslinking the adduct, and characterizing the adduct, where the active compound includes a hydroxamate moiety and a benzophenone photocrosslinking moiety.

According to another embodiment of the present invention, a method for determining the potency of an inhibitor against a metalloprotease is provided, the method including combining the inhibitor and an active compound with the metalloprotease to make a first sample, under conditions suitable for the formation of an active compound-metallohydrolase adduct, measuring the quantity of the adduct formed in the first sample, combining the active compound with the metalloprotease to make a control sample, under conditions suitable for the formation of the active compound-metalloprotease adduct to make a control sample, and determining the potency of the inhibitor as a degree of reduction of the quantity of the adduct formed in the first sample compared with the quantity of the adduct formed in the control sample, in a proportion to the quantity of the inhibitor used.

DETAILED DESCRIPTION OF THE INVENTION

Figure 1:
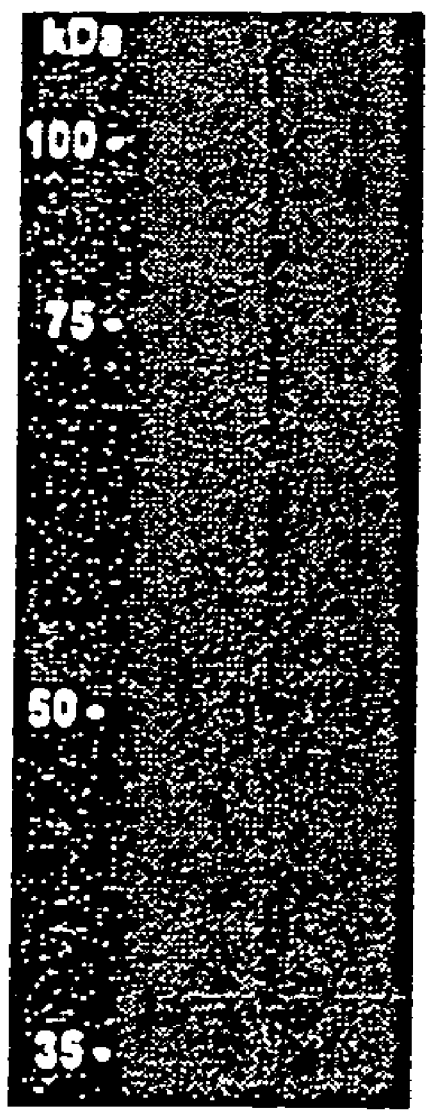
FIG. 1 shows the activity of a metalloprotease inhibitor in the presence of a rhodamine-tagged hydroxamate-benzophenone probe.

For the purposes of the present invention, the following terms, definitions and abbreviations apply:

The term "activity-based probes" sometimes abbreviated as "ABP" is defined as chemical reagents that are polyfunctional molecules for non-competitive or substantially irreversible binding to a target protein and inhibiting the action of the target protein.

The term an "active protein" is defined as any protein, incluiding any enzyme, in its normal wild-type conformation, e.g. a catalytically active state, as opposed to an inactive state. The active state allows the protein to function normally. An inactive state may be present as a result of any one or more chemical or biological process, such as, for example, denaturation, inhibitor binding, either covalently or non-covalently, mutation, secondary processing, e.g. phosphorylation or dephosphorylation, etc. Functional states of proteins or enzymes as described herein may be distinct from the level of abundance of the same proteins or enzymes.

The term "active site" with the reference to a protein is defined as the specific area on the surface of a protein, e.g., an enzyme molecule, to which a molecule can be bound to form a conjugate. An active site is an available wild-type conformation at a site that has biological activity, such as the catalytic site of an enzyme, a cofactor-binding site, the binding site of a receptor for its ligand, and the binding site for protein complexes.

The term "protein" is defined as a biological polymer comprising units derived from amino acids linked via peptide bonds; a protein can be composed of two or more chains.

The term "enzyme" is defined as a protein acting as a biological catalyst that is capable of accelerating specific chemical reactions without altering the direction or nature of the reaction and that itself remains unchanged in the process.

The term "metalloprotease" sometimes abbreviated as "MP" is defined as an enzyme that uses a metal-activated water, e.g., zinc-activated water, to catalyze the hydrolytic degradation of proteins or polypeptides to smaller amino acid polymers.

The term "proteome" is defined as the combination or the assembly of all the proteins expressed by a given organism, biological system, tissue or cell at a given time under given conditions.

The term "hydroxamate moiety" is defined as the chemical moiety derived from hydroxylamine and having the structure (I), abbreviated as "Hx":

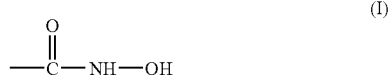

(I)

The term "benzophenone moiety" is defined as the moiety derived from diphenylketone and having the structure (II), abbreviated as "BP":

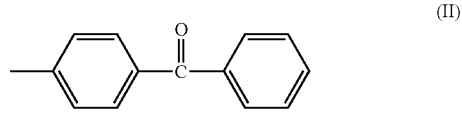

(II)

The term "crosslinking moiety" is defined as the moiety forming the bonds between adjacent chains in a protein.

The term "photocrosslinking moiety" is defined as the crosslinking moiety that is activated by radiation to form the bonds between adjacent chains in a protein The term "rhodamine moiety" is defined as the moiety having the structure (III), abbreviated as "Rh":

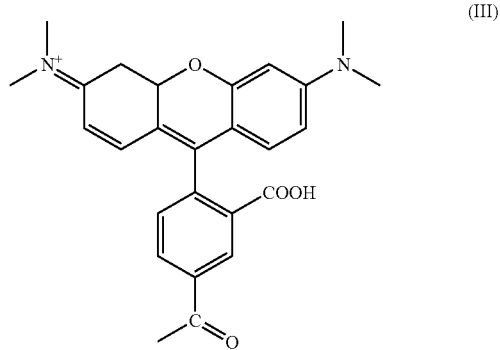

(III)

The term "biotin moiety" is defined as the moiety having the structure (IV), abbreviated as "Bio":

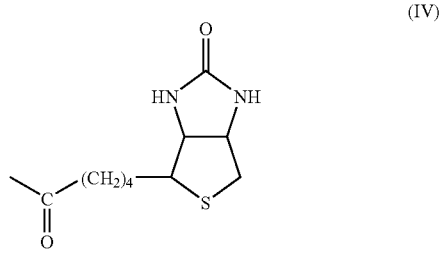

(IV)

The abbreviation "IC" means "inhibitory concentration" and the term abbreviated as "$IC_{50}$" is defined as a concentration of a compound needed to inhibit activity of 50% of an enzyme in a sample.

The following abbreviations are used to explain the multiplicities in the NMR spectra described below in the application: s=singlet, d=doublet, t=triplet, q=quartet, m=multiplet, b=broad.

The abbreviation "HBTU" stands for O-benotriazol-1-yl-N,N,N',N'-tetramethyluronium hexafluorophosphate.

The abbreviation "DIEA" stands for diisopropylethylamine.

The abbreviation "BOC" stands for N-tert-butoxylcarbonyl.

The abbreviation "Bpa" stands for 4-benzoyl-phenylalanine.

The abbreviation "EDC" stands for 1-(3-dimethylaminopropyl)-3-ethylcarbodiimide hydrochloride.

The abbreviation "$RhN_3$" stands for rhodamine-azide.

The abbreviation "$TriN_3$" stands for rhodamine-biotin-azide.

The abbreviation "EtOAc" stands for ethyl acetate.

The abbreviation "Hex" stands for any hexane.

The abbreviation "Aq" stands for aqueous.

The abbreviation "HxBP—Rh" stands for any compound including the following three moieties: hydroxamate moiety (I), benzophenone moiety (II) and rhodamine moiety (III). The abbreviation "HxBP—Rh-Bio" stands for any compound including the following four moieties: hydroxamate moiety (I), benzophenone moiety (II), rhodamine moiety (III), and biotin moiety (IV).

According to one embodiment of the present invention, activity-based probes (ABPs) for profiling zinc-depending enzymes are provided. One type of zinc-depending enzymes, for profiling of which ABPs of the present invention can be used, includes metalloproteases (MP). Activity-based probes are provided for specific reaction with an active site of one or more target MPs. The ABPs can comprise at least a reactive functionality and a ligand and have an affinity for a related group of proteins, whereby the ABP can bind to the target protein and substantially inactivate the protein, and the ligand canl permit detection and/or isolation.

The probes can be chemical compounds including hydroxamate moiety (I), e.g., a zinc-chelating hydroxamates moiety, and a benzophenone photocrosslinking moiety (II). The hydroxamate moiety can promote selective binding of the probe to the active sites of an MP. The benzophenone photocrosslinking moiety participates in the modification of the MP active sites. A general formula of a compound that can be used as the probe can be shown by formula (V):

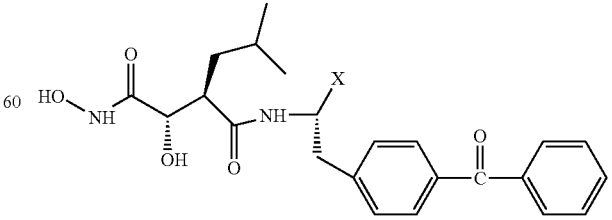

(V)

wherein X is a functional group.

Any MP can be profiled with the ABPs described above. Exemples of metallohydrolases that can be so profiled include matrix metalloproteinases ("MMPs"), e.g. MMP1-13, membrane type metalloproteinases, aminopeptidases, and metallopeptidases. One example of a metallopeptidase that can be profiled includes proteinase II, also known as zinc-endopeptidase or adamalysin.

According to embodiments of the inventions, ABPs can be used to profile the activity and inhibitor sensitivity of MPs in cell and tissue proteomes, resulting in the identification of MPs that are highly upregulated in invasive cancer cells. The probes can be also used for discovery of novel targets of MP inhibitors currently in clinical development.

In addition to the hydroxamate and the benzophenone moiety, the compounds used as ABPs can also include at least one other functional group. Examples of functional groups X (as shown in formula V) that can be used include a rhodamine group (III) and a biotin group (IV). Other functional moieties X that can be used include oligonucleotides, azides/alkynes (which allow for subsequent coupling to a variety of supports using cycloaddition chemistry), and p-nitrophenyl.

Examples of particular compounds that can be used include compounds of the HxBP—Rh group, such as a compound of any of the formulae (VI) (HxBP—Rh having rhodamine group), (VII) (also having rhodamine group), and (VIII) (HxBP—Rh-Bio, having both rhodamine group and biotin group), as shown below:

A variety of synthetic methods can be used to prepare the probes of this invention, i.e., compounds including hydroxamate moiety (I) and a benzophenone moiety (II). One method that can be used to synthesize HxBP—Rh (VII) and HxBP—Rh-Bio (VIII) can be schematically illustrated by the reaction Scheme A.

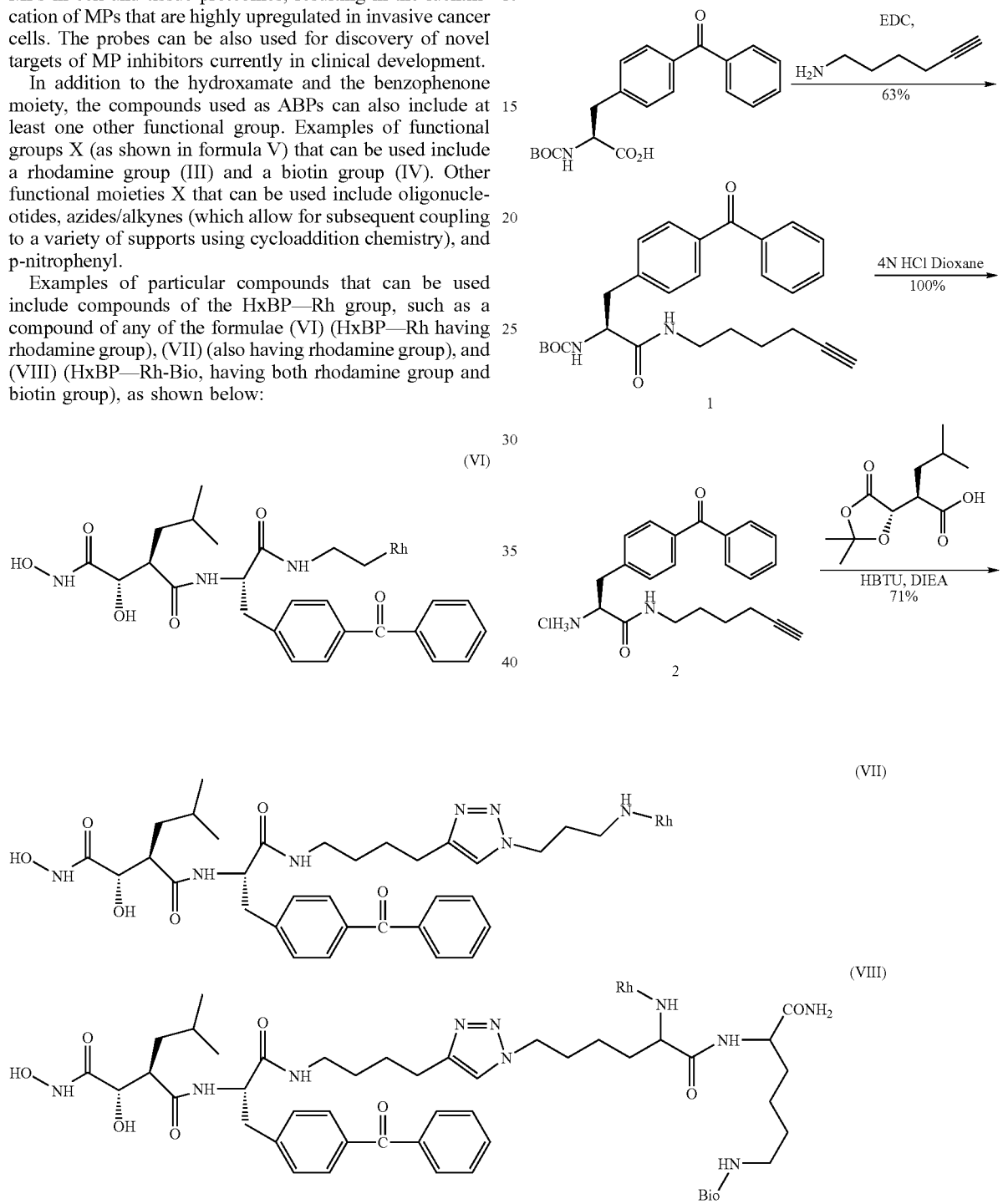

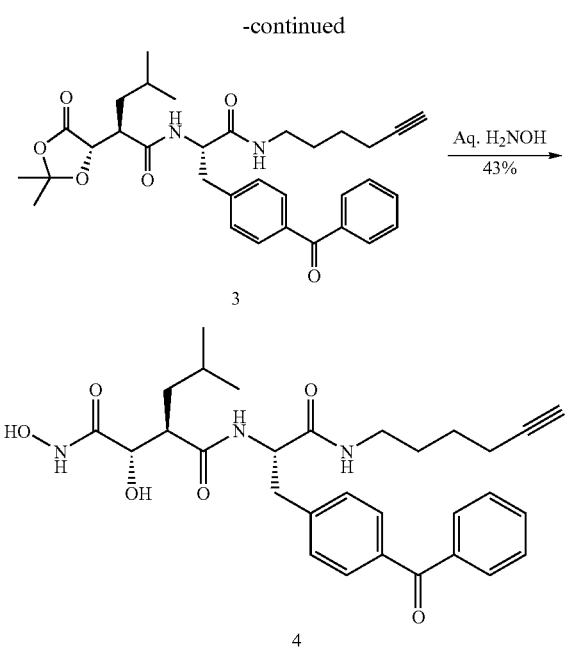

As shown by Scheme A, a protected amino acid having a benzophenone moiety can be coupled, in the presence of EDC, to an acetylenated amine. A suitable protective group can be selected by those having ordinary skill in the art. For example, a BOC group can be used. The product of the coupling 1 can be then de-protected by removing the BOC group, for example, using hydrochloric acid, to obtain product 2. The product 2 can be then reacted with a carboxylic acid in the presence of HBTU and DIEA, to obtain product 3. For example, a derivative of pentanoic acid can be used as the carboxylic acid, such as 2R-(2,2-dimethyl-4-oxo-1,3-dioxalan-5S-yl)-4-methylpentanoic acid.

Product 3 can be then reacted with aqueous hydroxylamine, to obtain product 4 having both hydroxamate moiety (I) and a benzophenone moiety (II). Product 4 can be then reacted with RhN$_3$ in the presence of copper sulfate and sodium ascorbate, to obtain a RxBP—Rh product (VII). Alternatively, product 4 can be reacted with TriN$_3$, instead of RhN$_3$, also in the presence of copper sulfate and sodium ascorbate, to obtain a RxBP—Rh-Bio product (VIII).

Alternatively, a method that can be also used to synthesize HxBP—Rh (VII) and HxBP—Rh-Bio (VIII) can be schematically illustrated by the reaction Scheme B.

Scheme B

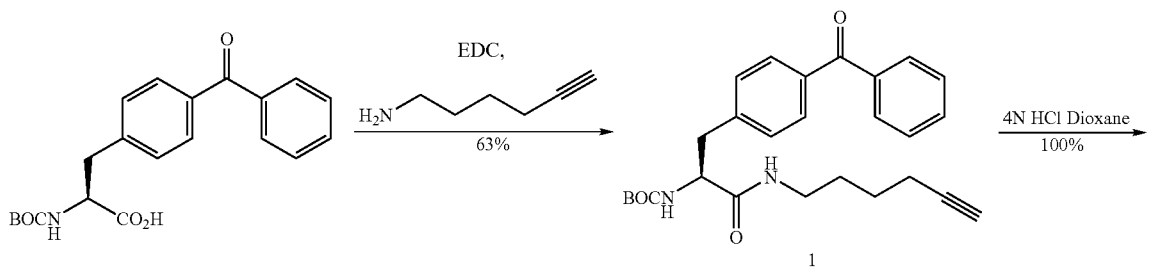

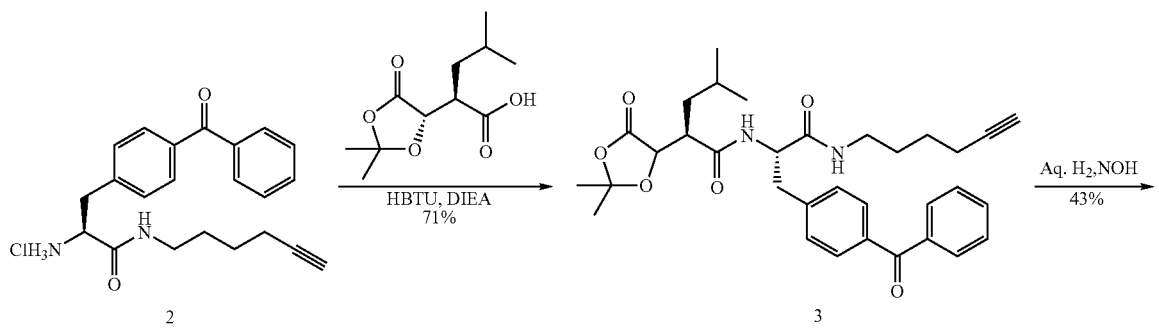

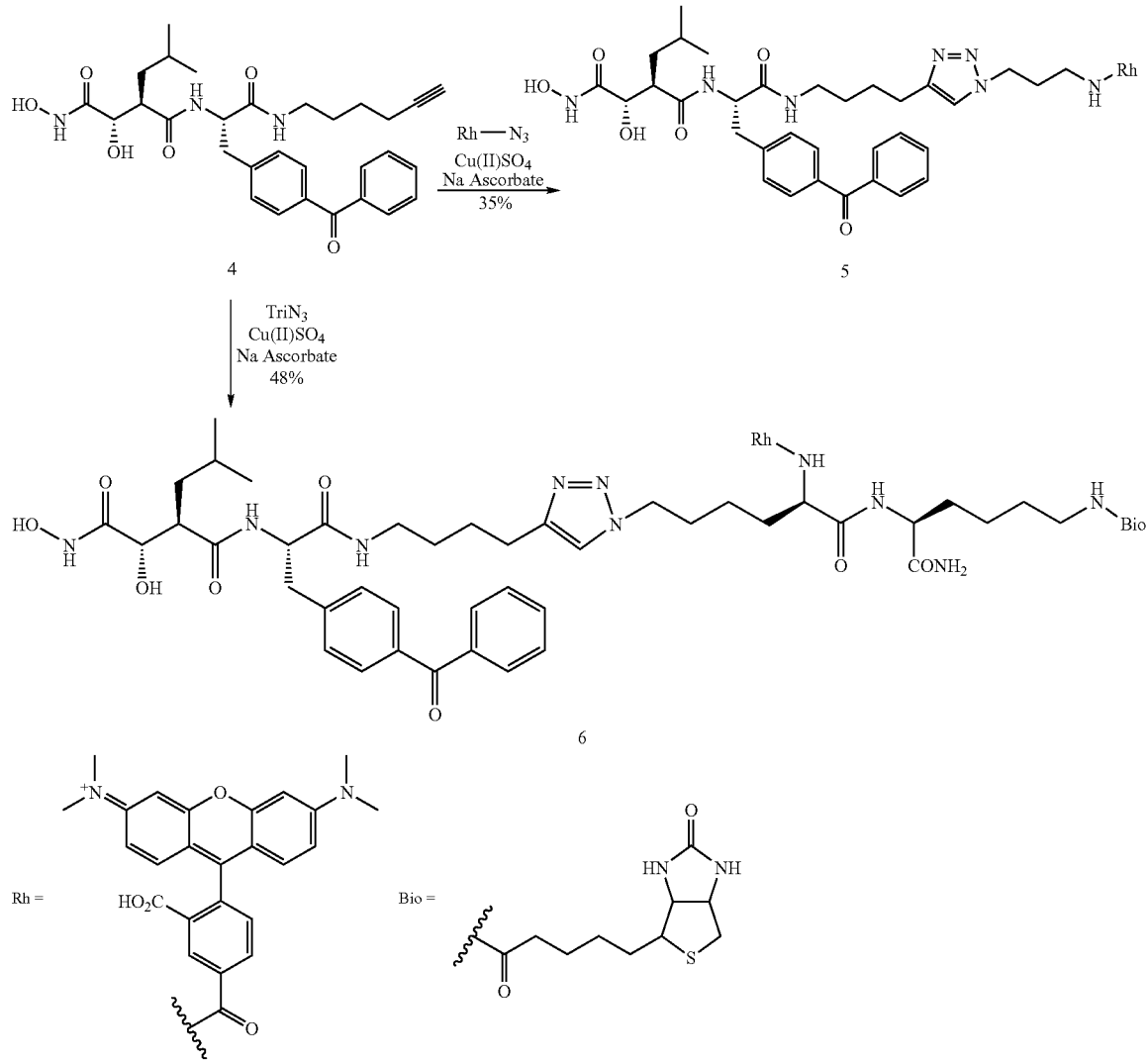

The final compounds are shown by the Scheme B, where RxBP—Rh compound (VII) is product 5, and RxBP—Rh-Bio compound (VIII), is product 6. The particular conditions under which the reaction Schemes A and B can be carried will be discussed below, in the "Examples" portion of the present application. Those having ordinary skill in the art can appreciate that the reaction Schemes A and B show only one exemplary synthesis. Other synthetic schemes can be devised and implemented to obtain the same final compounds, if desired.

A probe compound synthesized as described above can be then combined with a metalloprotease to form an adduct. The metalloprotease can be first isolated, or, if desired, the probe can be combined with the whole proteome sample containing the metalloprotease that is the subject of the analysis and profiling.

Following the formation of the adduct, the adduct can then be crosslinked utilizing the benzophenone crosslinking moiety of the probe compound. Following the crosslinking, the adduct can be analyzed and the metalloprotease profiled. The conditions that are suitable for forming the adduct and for the crosslinking thereof can be selected by those having ordinary skill in the art. For example, the conditions described in more detail in the "Examples" portion of the application can be used.

Any suitable method can be used for the profiling and the analysis. A particular method to be used can be selected by those having ordinary skill in the art. Examples of some analytical or profiling techniques that can be used include fluorescence, labeling and scanning, in-gel visualization, measurement of $IC_{50}$ values, and mass spectroscopy. Mass spectroscopy can be used in tandem with microcapillary liquid chromatography-electrospraying.

For example, for conducting an analysis of the inhibition of matrix metalloproteinases using HxBP—Rh, the following technique can be used. The substrate, DABCYL-Gaba-ProAsnGlyLeuGlu-EDANS, and purified MMPs (MMP-2, MMP-7, MMP-9) can be obtained from EMD Biosciences. The assay buffer can be used having pH 7.5, and including 100 mM Tricine, 100 mM NaCl, 10 mM $CaCl_2$, 50 mM $ZnCl_2$, and 0.005% Brij 35. Final concentrations of the components in the assay buffer can be 0.5 ng of MMP, 12.5 mM of substrate, and 0 to 5000 nM of HxBP—Rh. Fluorescence measurements (excitation 340 nm and emission 465 nm) can be performed using a GENios fluorescence plate reader from Tecan instruments. Reactions can be initiated by adding the substrate last to the mixture and measuring the fluorescence increase every 2 minutes for 1 hour.

For labeling and detection of MPs using HxBP—Rh, the following technique can be used. Purified MMP-2 can be diluted in buffer 1 (30 ng of enzyme) and mixed with 100 nM HxBP—Rh in the presence or absence of 5 µM GM6001 or TIMP-1 (80 ng). These mixtures can be pre-incubated on ice for 15 min prior to irradiation at 365 nm for 1 hour (on ice) followed by quenching with one volume of standard 2× SDS/PAGE loading buffer (reducing). Kidney and cancer cell proteomes, prepared as known to those having ordinary skill in the art, can be adjusted to 1 mg/ml in 50 mM Tris-HCl buffer (pH 8.0) prior to labeling. A portion of each cancer cell line proteome sample can be treated with PNGaseF (New England Biolabs) to provide deglycosylated proteomes, as known to those having ordinary skill in the art. Labeled samples can be separated by SDS-PAGE, and visualized in-gel with a Hitachi FMBio IIe flatbed scanner (Mirabio). Integrated band intensities can be calculated from several independent labeling reactions, and averaged to provide the level of each enzyme activity in each sample.

For isolation and molecular characterization of HxBP—Rh-labeled proteins, the following technique can be used. A trifunctional-HxBP—Rh-Bio probe (biotin and rhodamine coupled) can be used. An avidin-based affinity purification procedure can be employed as known to those having ordinary skill in the art. Avidin enriched probe-labeled proteins can be separated by SDS-PAGE and protein bands can be excised and digested with trypsin (Promega). The resulting peptide mixture can be then analyzed by microcapillary liquid chromatography-electrospray tandem mass spectrometry combined with a Deca mass spectrometer. The MS data can be used to search public databases to identify the HxBP-labeled proteins.

For measuring the $IC_{50}$ values for MP inhibitors using HxBP—Rh, the following technique can be used. $IC_{50}$ values for neprilysin, dipeptidylpeptidase III (DPPIII), and leucine aminopeptidase (LAP) can be determined using Prism Software (Graph Pad) from dose-response curves of three trials at concentrations of GM6001 ranging from 0.001-20 µM and 50 nM HxBP—Rh probe. Neprilysin, DPPIII, and LAP assays can be conducted using MUM-2B membrane, MCF7 soluble, and mouse kidney soluble proteomes, respectively.

One analytical technique that can be used can be directed to the determination of the potency of an inhibitor against a particular metalloprotease. According to this method, an activity-based probe compound of the present invention can be combined with metalloprotease proteome and an inhibitor, under conditions suitable to forming the active compound/metalloprotease adduct, to make a first sample. Any inhibitor known to inhibit the particular metalloprotease, to be selected by those having ordinary skill in the art, can be employed. The amount the adduct present in the first sample can be measured.

A control sample can then be made by combining metalloprotease proteome and the activity-based probe compound without the inhibitor, under conditions suitable to forming the active compound/metalloprotease adduct, and the amount of the adduct obtained in the control sample can be also measured. The amounts of the adduct obtained in the first sample and the control sample can then be compared.

In the first sample the inhibitor is expected to bind to a portion of the metalloprotease, rendering this portion incapable of reacting with the active compound of the probe. Therefore, a reduction of the signal intensity from the reporter group in the first sample is expected, in comparison with the signal intensity in the control sample. The more potent the inhibitor, the higher degree of reduction is expected. Thus, the potency of the inhibitor can be determined by the reduction of the signal intensity, indicative of the amount of the active compound/metalloprotease adduct obtained, in a proportion of the quantity of the inhibitor used.

The concept of studying the inhibitors can be further illustrated by FIG. 1, which shows that HxBP—Rh identifies dipeptidylpeptidase III (DPPIII) as a GM6001-sensitive metalloprotease present in the human breast cancer cell line MCF7. Shown is a representative HxBP—Rh labeling (100 nM) profile of the soluble proteome from MCF-7 cells. The labeling of an ~80 kDa protein was blocked by GM6001 (5 µM) and this target was identified using a trifunctional-HxBP probe as dipeptidylpeptidase III (DPPIII) (single arrowhead).

The invention will now be described in greater detail by reference to the following non-limiting examples.

EXAMPLES

Example 1

Synthesis of RxBP—Rh and RxBP—Rh-Bio Compounds

This example illustrates one way of preparing RxBP—Rh and RxBP—Rh-Bio compounds.

General Synthetic Techniques. All chemicals were purchased from commercial sources (Aldrich, Acros, Novabiochem, Molecular Probes) and were used without further purification. Dry tetrahydrofuran (THF), dimethylformamide (DMF), and methylene chloride ($CH_2Cl_2$) were obtained by passing commercially available pre-dried, oxygen-free formulations through activated alumina columns. Reactions were monitored by thin-layer chromatography (TLC) carried out on Whatman silica gel plates (cat. No. 4861-820) using UV light as the visualizing agent. LC/MS using an Agilent 1100 MSD was used to monitor those reactions that were not amenable to TLC analysis. Silica gel chromatography was performed using EMD silica gel 60 (cat. No. 11567-1). HPLC was performed using a Hitachi L-7150 pump equipped with a Higgins Analytical C18, 5 µm, 150×10 mm reverse phase column. Purifications were achieved using a binary gradient with A: 95/5 $H_2O$/ACN 0.05% TFA and B: 95/5 ACN/$H_2O$ 0.05% TFA with a flow rate of 5 mL/min. $^1H$ NMR spectra were recorded on a Bruker AMX500 MHz spectrometer. Chemical shifts are reported in δ ppm values relative to the DMSO (2.49 ppm) and coupling constants (J) are reported in Hz. Below, all numerals identifying particular compounds are with the reference to the reaction Schemes A and B.

Preparation of $N^1$-Boc-Bpa-$N^2$-hexyneamide (1). To a vial containing N-Boc-Bpa-OH, 120 mg, 0.325 mmole, 1 eq.) and 1-amino-hex-5-yne (38 mg, 0.395 mmole, 1.2 eq.) was added 5 mL of methylene chloride followed by EDC (124 mg, 0.650 mmole, 2 eq.). After stirring overnight the reaction was diluted with 20 mL of methylene chloride and washed once with 10% HCl and once with brine. The organic layer was dried using $Na_2SO_4$ and concentrated under reduced pressure using a rotary evaporator. Column chromatography (ethyl acetate) afforded 1 as a white solid (92 mg, 63%). $^1H$ NMR (500 MHz, DMSO) δ 7.90 (b, 1 H), 7.69 (d, 2H, J=7.7 Hz), 7.65 (m, 3H), 7.55 (t, 2H, J=7.3 Hz), 7.42 (d, 2H, J=8.1 Hz), 6.96 (d, 2H, J=8.45 Hz), 4.17 (m, 1H), 3.04 (m, 3H), 2.83 (m, 1H), 2.71 (s, 1H), 2.13 (m, 2H), 1.41(m, 4H), 1.30 (s, 9H). MALDI-FTMS m/z 471.2244 ($C_{27}H_{32}N_2O_4$+Na requires 471.2254).

Preparation of $N^1$-4-Bpa-$N^2$-hexyneamide (2). 4.0 N HCl in dioxane (2 mL) was added to a vial containing 1 (56 mg, 0.124 mg, 1 eq.). After 4 hours, the solvent was evaporated under reduced pressure using a rotary evaporator and placed under vacuum overnight to give 2 (43 mg, quantitative). $^1$H NMR (500 MHz, DMSO) δ 8.49 (t, 1 H, J=5.5 Hz), 8.32 (s, 3H), 7.70 (m, 5H), 7.57 (t, 2H, J=7.7 Hz), 7.42 (d, 2H, J=8.1 Hz), 3.99 (t, 1H, J=7.1 Hz), 3.12 (m, 3H), 2.98 (m, 1H), 2.72 (t, 1H, J=2.55 Hz), 2.09 (m, 2H), 1.35 (m, 4H). MALDI-FTMS m/z 349.1922 ($C_{22}H_{25}N_2O_2$+. requires 349.1911).

Preparation of $N^2$-[2R-(2,2-dimethyl-4-oxo-1,3-dioxalan-5S-yl)-4-methylpentanoyl]-L-4-Bpa-$N^1$-hexyneamide (3). 2R-(2,2-Dimethyl-4-oxo-1,3,-dioxalan-5S-yl)-4-methyl-pentanoic acid (40 mg, 0.173 mmole, 1 eq.) was dissolved in anhydrous DMF. This was followed by the addition of 2 (67 mg, 0.2 mmole, 1.1 eq.), HBTU (66 mg, 0.173 mmole, 1 eq.), and DIEA (100 μL). After 1 hour the reaction was diluted in ethyl acetate (25 mL) and washed twice with 10% HCl. The organic layer was then dried with $Na_2SO_4$ and concentrated under reduced pressure using a rotary evaporator. The residue was placed under vacuum to remove any residual DMF prior to chromatography. Column chromatography (50/50 EtOAc:Hex) afforded 3 as a gummy white solid (69 mg, 71%). $^1$H NMR (500 MHz, DMSO) δ 8.20 (d, 1 H, J=8.45), 7.89 (t, 1H, J=5.5 Hz), 7.66 (m, 5H), 7.55 (t, 2H, J=7.7 Hz), 7.39 (d, 2H, J=8.1 Hz), 4.60 (m, 1H), 4.43 (d, 1H, J=8.45), 2.93 (m, 1H), 2.72 (m, 2H), 2.11 (m, 2H), 1.48 (m, 2H), 1.38 (m, 11H), 0.83 (d, 3H, J=6.6 Hz), 0.80 (d, 3H, J=6.6 Hz). MALDI-FTMS m/z 561.2950 ($C_{27}H_{32}N_2O_4$+H requires 561.2959).

Preparation of $N^1$-[3S-Hydroxy-4-(N-hydroxyamino)-2R-isobutylsuccinyl-L4-benzoyl-phenylalanine-$N^1$-hexyneamide (4). THF (7 mL) was added to a round bottom flask containing 3 (29.5 mg, 0.05 mmole) followed by hydroxylamine (1.5 mL of a 50% solution in water). This solution was then refluxed at 80° C. for 1 hour at which time no starting material was visible by TLC (EtOAc). The reaction was then concentrated under reduced pressure using a rotary evaporator. This residue was then purified by HPLC (gradient 10-40% B over 60 minutes product elutes at 39.5 minutes) to afford 4 (12 mg, 43%) as a white film. $^1$H NMR (500 MHz, DMSO) δ 10.60 (s, 1H), 8.84 (s, 1H), 7.98 (d, 1 H, J=8.4), 7.87 (t, 1H, J=5.5 Hz), 7.66 (m, 5H), 7.55 (t, 2H, J=7.7 Hz), 7.39 (d, 2H, J=7.7 Hz), 5.47 (b, 1H), 4.49 (m, 1H), 3.78 (d, 1H, J=7.4 Hz), 3.05 (m, 4H), 2.7 (s, 1H), 2.56 (m, 1H), 2.19 (m, 2H), 1.45 (m, 5H), 1.30 (b, 2H), 0.82 (d, 3H, J=6.3 Hz), 0.79 (d, 3H, J=6.2 Hz). MALDI-FTMS m/z 536.2745 ($C_{30}H_{37}N_3O_6$+H requires 536.2755).

Preparation of HxBP—Rh (5). A fresh solution of sodium ascorbate (200 mg/mL, 100 μL) and copper (II) sulfate (85 mg/mL, 30 μL) was added to a mixture of 4 (9.5 mg, 0.02 mmole, 1 eq.) and RhN3 (5 mg, 0.01 mg, 0.5 eq.) in 300 μL of methanol and 70 μL water. The reaction was stirred vigorously for 1 hour and concentrated under reduced pressure using a rotary evaporator. The residue was then taken up in DMF and purified by HPLC (gradient 10-80% B over 60 minutes product elutes as a very broad peak between 30-38 minutes and LC/MS was used to identify the product containing fractions) to afford 5 (3.5 mg, 35%) as a dark red film. MALDI-FTMS m/z 1048.4886 ($C_{30}H_{37}N_3O_6$+. requires 1048.4927).

Preparation of trifunctional product HxBP—Rh-Bio (6). A fresh solution of sodium ascorbate (200 mg/mL, 100 μL) and copper (II) sulfate (85 mg/mL, 30 μL) was added to a mixture of 4 (4 mg, 0.008 mmole, 1 eq.) and $TriN_3$ (4 mg, 0.004 mg, 0.5 eq.) in 300 μL of methanol and 70 μL water. The reaction was stirred vigorously for 1 hour and concentrated under reduced pressure using a rotary evaporator. The residue was then taken up in DMF and purified by HPLC (gradient 10-75% B over 35 minutes product elutes at 15 minutes and LC/MS was used to identify the product containing fractions) to afford 6 (3 mg, 48%) as a dark red film. MALDI-FTMS m/z 1463.6978 ($C_{30}H_{37}N_3O_6$+. requires 1473.7024).

Example 2

Activity-Based Labeling of Purified MMP-2 Using the Compounds of the Present Invention This example illustrates one way of labeling of a metalloprotease using the RxBP—Rh compound.

Figure 2:
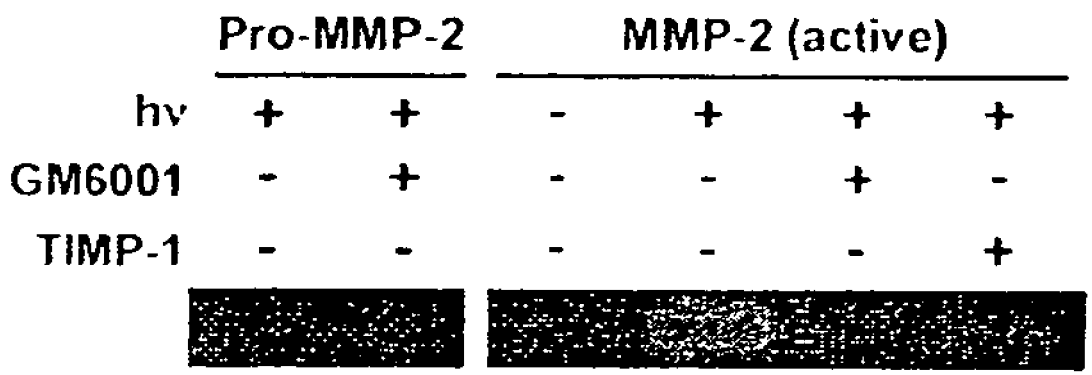
FIG. 2 shows activity-based labeling of a purified metalloprotease by a rhodamine-tagged hydroxamate-benzophenone probe.
Figure 2:
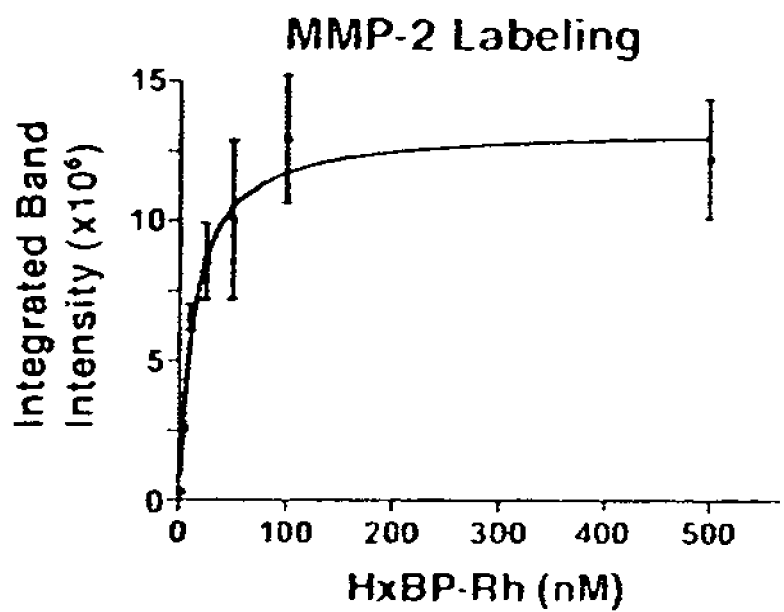

With the reference to FIG. 2A, 50 nM HxBP—Rh was incubated with purified samples of pro-MMP-2 (30 ng) or MMP-2 (30 ng) with or without inhibitors [GM6001 (5 μM) or TIMP-1 (80 ng)] for 15 min prior to photocrosslinking by exposure to UV-light. Samples were then analyzed by SDS-PAGE and in-gel fluorescence scanning. HxBP—Rh labeled active MMP-2, but not pro-MMP-2 or inhibitor-bound MMP-2.

FIG. 2B shows the concentration dependence of MMP-2 labeling by HxBP—Rh. Labeling of MMP-2 was saturated at ~100 nM HxBP—Rh. Labeling was measured by in-gel fluorescence scanning (integrated band intensities are given in arbitrary units). Each data point corresponds to the average of two independent trials.

Example 3

Activity-Based Labeling of Purified MMP-2 in Whole Proteomes Using the Compounds of the Present Invention This example illustrates another way of labeling of a metalloprotease using the RxBP—Rh compound.

Figure 3:
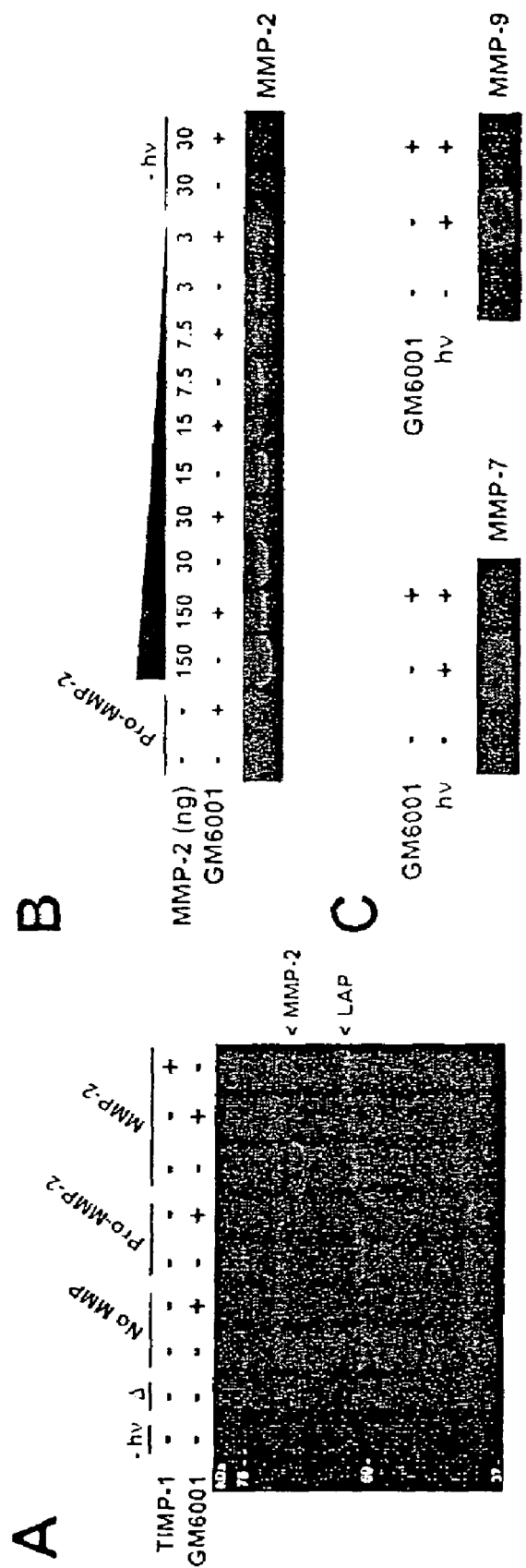
FIG. 3 shows activity-based labeling of a purified metalloprotease by a probe in whole proteome.

With the reference to FIG. 3A, purified MMP-2 (100 ng) or pro-MMP-2 (100 ng) were added to a mouse kidney proteome (15 μL, 1 μg protein/μL) and treated with HxBP—Rh (100 nM) for 15 min prior to photocrosslinking and analysis by SDS-PAGE and in-gel fluorescence scanning. Only MMP-2 was labeled by HxBP—Rh and this labeling was blocked by GM6001 (5 μM) and TIMP-1 (200 ng). No protein labeling was observed in the absence of exposure to UV light. Also highlighted in this profile is an endogenous GM6001-sensitive enzyme activity labeled by HxBP—Rh, which was identified using a trifunctional HxBP probe as leucine aminopeptidase (LAP).

FIG. 3B illustrates HxBP—Rh labeling of a serial dilution of purified MMP-2 added to a mouse kidney proteome. HxBP—Rh could detect as low as 3 ng of active MMP-2 (corresponding to 3 nM enzyme in a background of 15 μL of 1 μg/μL proteome). HxBP—Rh did not label pro-MMP-2 (150 ng).

FIG. 3C demonstrates HxBP—Rh labeling of MMP-7 and MMP-9 in proteomes. MMP-7 and MMP-9 (30 ng) were added to the mouse kidney proteome (15 μL, 1 μg/μL) and the samples were treated with HxBP—Rh (100 nM) and analyzed as described above. HxBP—Rh labeled active, but not GM6001-inhibited MMP-7 and MMP-9.

Example 4

Metalloprotease Identification Using the Compounds of the Present Invention This example illustrates one way of identifying of a metalloprotease using the RxBP—Rh compound, and demonstrates that HxBP—Rh identifies neprilysin as an MP activity dramatically upregulated in invasive human melanoma cell lines.

Figure 4:
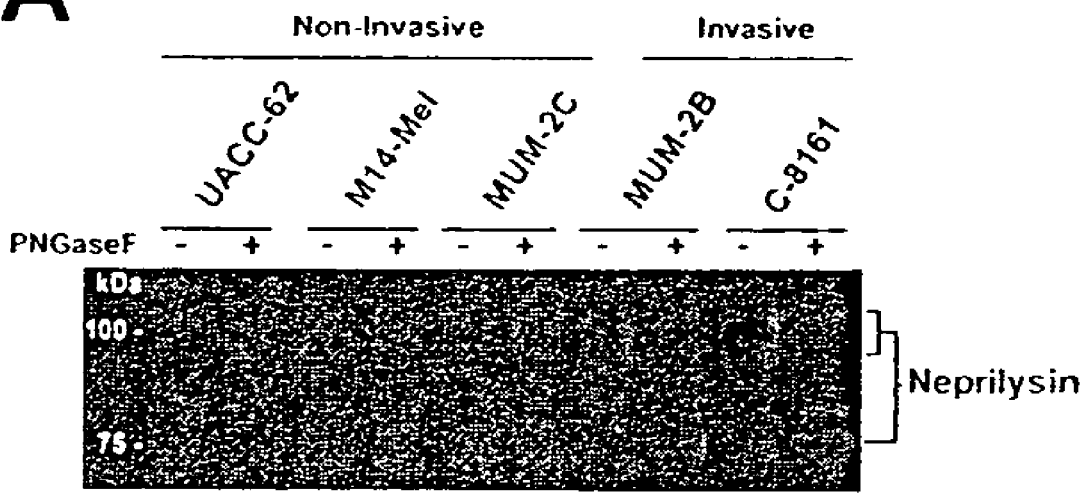
FIG. 4 shows activity-based labeling of various metalloproteases.
Figure 4:
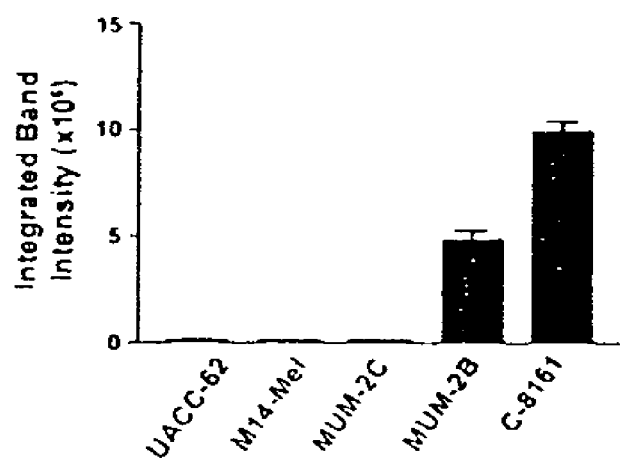

With the reference to FIG. 4A, HxBP—Rh labeling profiles of membrane proteomes from a panel of human melanoma cell lines are shown. An HxBP—Rh-labeled glycoprotein highly upregulated in invasive melanoma lines (MUM-2B and C-8161) compared to non-invasive melanoma lines (UACC62, M14-MEL, and MUM-2C) was identified using a trifunctional HxBP probe as neprilysin. Deglycoslyation was accomplished by treating a portion of each HxBP—Rh-labeled proteome with PNGaseF prior to analysis.

Figure (B illustrates quantization of neprilysin activity in melanoma membrane proteomes by in-gel fluorescence scanning (n=3/group).

Example 5

Metalloprotease Identification Using the Compounds of the Present Invention

This example illustrates another way of identifying of a metalloprotease using the RxBP—Rh compound.

Figure 5:
FIG. 5 shows activity-based labeling of various metalloproteases.
Figure 5:
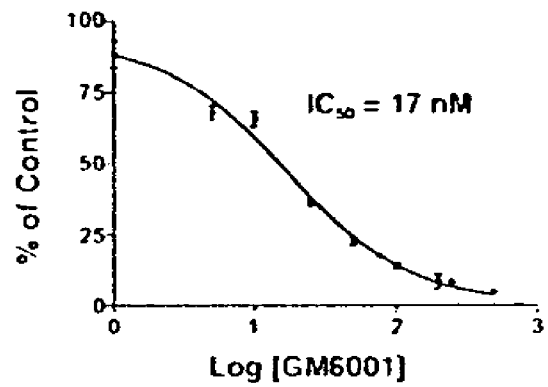
Figure 5:
Figure 5:
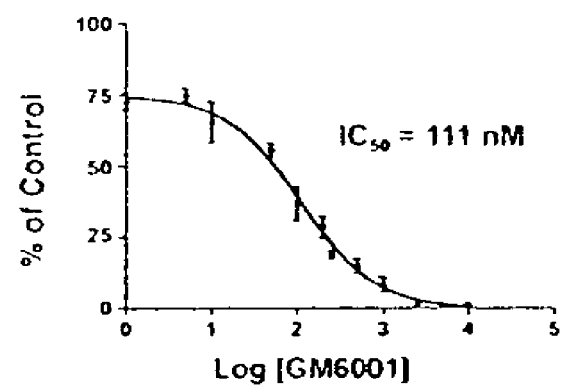
Figure 5:
Figure 5:
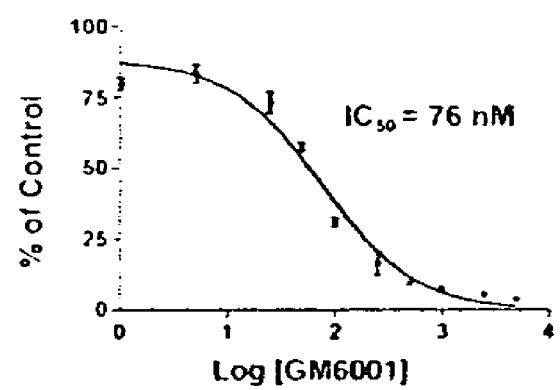

With the reference to FIG. 5, it is shown that HxBP—Rh identifies several MPs outside of the MMP family that are inhibited by GM6001, including neprilysin (A), leucine aminopeptidase (LAP) (B), and dipeptidylpeptidase III (DP-PIII) (C). Left panels show representative labeling of MPs in whole proteomes by HxBP—Rh (100 nM) and inhibition by GM6001 (5 µM). PNGaseF lanes are not shown for LAP and DPPIII because treatment with this glycosidase did not alter the migration of these MPs by SDS-PAGE. Neprilysin was identified in the secreted proteome of invasive human melanoma cell lines (see FIG. 4), while LAP and DPPIII were identified in soluble proteomes from mouse kidney, as shown by FIG. 3(A), and the human breast cancer cell line MCF7, respectively. Right panels show the concentration-dependence of inhibition of HxBP—Rh labeling of by GM6001 (each data point corresponds to the average of three independent trials and is presented as a percentage of control reactions conducted without GM6001). From these curves, $IC_{50}$ values of 17 nM (12-23 nM, 95% confidence limits), 111 nM (83-149 nM, 95% confidence limits), and 76 nM (53-109 nM, 95% confidence limits), were calculated for the inhibition of neprilysin, LAP, and DPPIII, respectively, by GM6001.

Although the invention has been described with reference to the above examples, it will be understood that modifications and variations are encompassed within the spirit and scope of the invention. Accordingly, the invention is limited only by the following claims.

What is claimed is:

1. A composition for analyzing metalloproteases, the composition comprising a chemical compound including a hydroxamate moiety and a benzophenone moiety, wherein the compound further includes at least one additional functional moiety selected from the group consisting of rhodamine, oligonucleotides, azides, alkynes, and p-nitrophenyl.

2. The composition of claim 1, wherein the hydroxamate moiety is a zinc-chelating hydroxamate moiety.

3. The composition of claim 1, wherein the metalloproteases comprise matrix metalloproteinases, membrane type metalloproteinases, aminopeptidases, or metallopeptidases.

4. The composition of claim 1, wherein the compound further includes a biotin group.

5. The composition of claim 1, wherein the metalloproteases are contained in a proteomic mixture of proteins from a cell.

6. A composition for analyzing metalloproteases, the composition comprising a chemical compound having the formula (I):

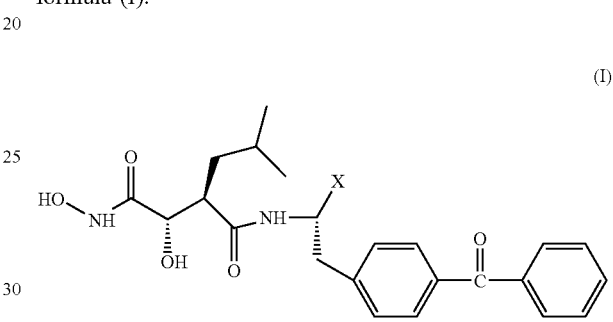

wherein X is a functional moiety, and wherein said compound (I) is a probe capable of reacting with said metalloproteases to form a probe/metalloprotease adduct.

7. The composition of claim 6, wherein the metalloproteases comprise matrix metalloproteinases, membrane type metalloproteinases, aminopeptidases, or metallopeptidases.

8. The composition of claim 6, wherein X includes a rhodamine group.

9. The composition of claim 8, wherein X further includes a biotin group.

10. The composition of claim 6, wherein X is selected from a group consisting of oligonucleotides, azides, alkynes, and p-nitrophenyl.

11. The composition of claim 6, wherein the chemical compound has the formula selected from a group consisting of formulae (II) and (III):

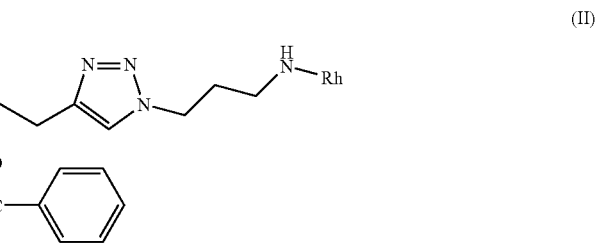

-continued

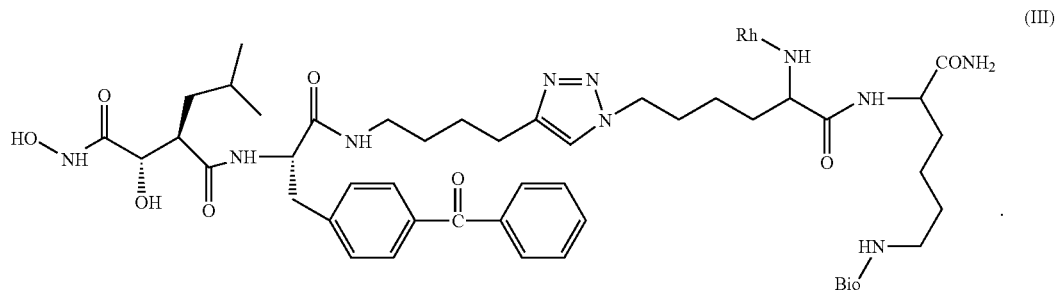
(III)

12. The composition of claim 6, wherein the metalloproteases are contained in a proteomic mixture of proteins from a cell.

13. A composition for analyzing metalloproteases, the composition comprising a chemical compound (I)

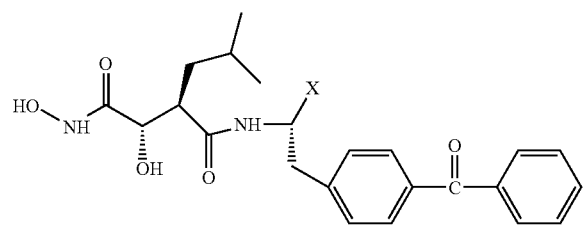
(I)

wherein X is a functional moiety.

14. The composition of claim 13, wherein the metalloproteases comprise matrix metalloproteinases, membrane type metalloproteinases, aminopeptidases, or metallopeptidases.

15. The composition of claim 13, wherein the metalloproteases are contained in a proteomic mixture of proteins from a cell.

16. The composition of claim 13, wherein X includes a rhodamine group.

17. The composition of claim 16, wherein X further includes a biotin group.

18. The composition of claim 13, wherein X is selected from a group consisting of oligonucleotides, azides, alkynes, and p-nitrophenyl.

19. A composition for analyzing metalloproteases, the composition comprising a chemical compound selected from a group consisting of compound (II) and (III):

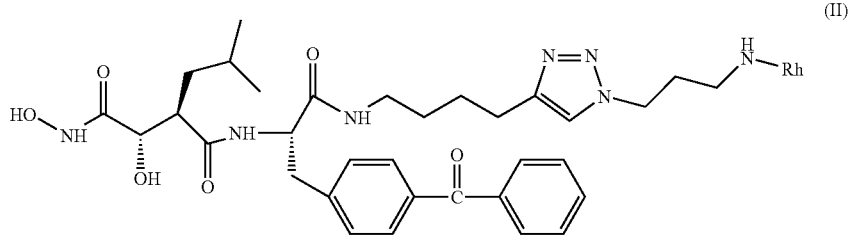
(II)

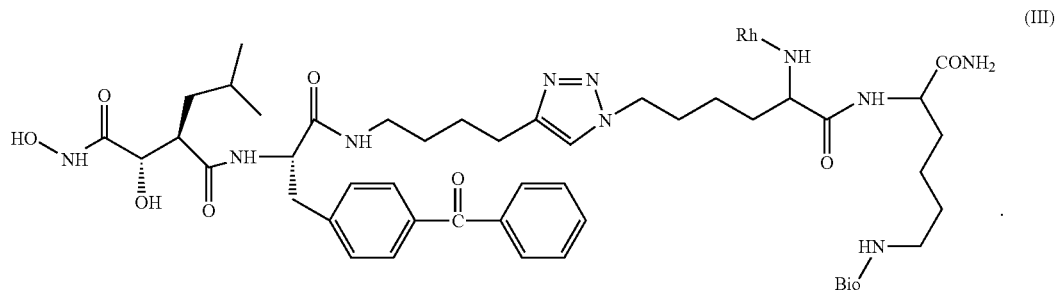
(III)

20. The composition of claim 19, wherein the metalloproteases comprise matrix metalloproteinases, membrane type metalloproteinases, aminopeptidases, or metallopeptidases.

21. The composition of claim 19, wherein the metalloproteases are contained in a proteomic mixture of proteins from a cell.

* * * * *